US011712563B2

(12) United States Patent
Park et al.

(10) Patent No.: US 11,712,563 B2
(45) Date of Patent: Aug. 1, 2023

(54) SOUND SOURCE SIGNAL SEPARATOR AND MUSIC SYNC LOW FREQUENCY STIMULATOR COMPRISING THE SAME

(71) Applicant: CERAGEM CO., LTD., Cheonan-si (KR)

(72) Inventors: Yong son Park, Anyang-si (KR); Dong Myoung Lee, Anyang-si (KR); Yong Hee Kim, Cheonan-si (KR); Seung Gwan Hong, Cheonan-si (KR)

(73) Assignee: CERAGEM CO., LTD., Cheonan-si (KR)

( * ) Notice: Subject to any disclaimer, the term of this patent is extended or adjusted under 35 U.S.C. 154(b) by 243 days.

(21) Appl. No.: 17/112,506

(22) Filed: Dec. 4, 2020

(65) Prior Publication Data

US 2021/0170171 A1 Jun. 10, 2021

(30) Foreign Application Priority Data

Dec. 6, 2019 (KR) .................. 10-2019-0161617

(51) Int. Cl.
*G06F 3/01* (2006.01)
*A61N 1/36* (2006.01)
*A61N 1/04* (2006.01)
*H04R 3/00* (2006.01)

(52) U.S. Cl.
CPC ........ *A61N 1/36034* (2017.08); *A61N 1/0492* (2013.01); *G06F 3/016* (2013.01); *H04R 3/00* (2013.01)

(58) Field of Classification Search
CPC .................. H04R 3/00; G06F 3/016

USPC .................. 381/58–59, 123, 98, 77, 80
See application file for complete search history.

(56) References Cited

U.S. PATENT DOCUMENTS

| 6,593,809 | B2* | 7/2003 | Hahn ............... | H04R 5/04 330/69 |
| 9,584,908 | B2* | 2/2017 | Ookuri ............ | H04R 3/002 |
| 9,881,467 | B2* | 1/2018 | Levesque ......... | G08B 6/00 |
| 10,620,704 | B2* | 4/2020 | Rand ............... | G06F 3/167 |
| 10,832,537 | B2* | 11/2020 | Doy ................ | H04R 3/00 |
| 11,269,415 | B2* | 3/2022 | Harvey ........... | G06F 3/016 |

(Continued)

FOREIGN PATENT DOCUMENTS

| KR | 10-2004-0009619 A | 1/2004 |
| KR | 10-2006-0125442 A | 12/2006 |

(Continued)

OTHER PUBLICATIONS

International Search Report of PCT Application No. PCT/KR2020/017579—2 pages (dated Jun. 2, 2021).

(Continued)

*Primary Examiner* — Disler Paul
(74) *Attorney, Agent, or Firm* — Knobbe, Martens, Olson & Bear, LLP

(57) ABSTRACT

A music sync low frequency stimulator can includes a speaker for outputting a plurality of first sound source signals, a sound source signal separator for separating at least one of the plurality of first sound source signals, a low frequency signal generator for generating a low frequency signal, and a music sync unit for controlling the strength and frequency of a low frequency signal according to at least one of second sound source signals separated by the sound source signal separator.

18 Claims, 3 Drawing Sheets

(56) References Cited

U.S. PATENT DOCUMENTS

2015/0343214 A1  12/2015  Yamazaki
2019/0107891 A1* 4/2019  Rank ................ H04N 21/23614

FOREIGN PATENT DOCUMENTS

| KR | 10-0846179 B1     | 7/2008 |
|----|-------------------|--------|
| KR | 10-2012-0002791 A | 1/2012 |
| KR | 10-2012-0066388 A | 6/2012 |
| KR | 10-1256565 B1     | 4/2013 |
| KR | 10-2019-0004483 A | 1/2019 |

OTHER PUBLICATIONS

Office Action of Korean Patent Application No. 10-2019-0161617—17 pages (dated Jul. 1, 2021).

* cited by examiner

SOUND SOURCE SIGNAL SEPARATOR AND MUSIC SYNC LOW FREQUENCY STIMULATOR COMPRISING THE SAME

CROSS-REFERENCE TO RELATED APPLICATION

This application claims priority to and the benefit of Korean Patent Application No. 10-2019-0161617, filed on Dec. 6, 2019, the disclosure of which is incorporated herein by reference in its entirety.

BACKGROUND

Technical Field

The present disclosure relates to a sound source signal separator and a music sync low frequency stimulator including the same.

Discussion of Related Technology

Recently, a low frequency stimulator has been developed that promotes blood circulation in the human body using low frequency stimulation.

A low frequency stimulator generates a low frequency wave and Outputs the same to an electrode pad, and when the electrode pad contacts the human body, low frequency stimulation is transmitted to the human body.

Such a low frequency stimulator is used to achieve a therapeutic effect by contacting an electrode pad to the acupuncture points of the human body or a region where muscle pain is felt.

The disclosure of this section is to provide background information relating to the invention. Applicant does not admit that any information contained in this section constitutes prior art.

SUMMARY

Low frequency stimulators may generate low frequency waves in accordance with a predetermined pattern and transmit the same to the human body. However, would be difficult to achieve a therapeutic effect if it is used for a long period of time because it is rather boring.

The present disclosure is directed to providing a sound source signal separator that can reduce body weight, beautify the body, and make metabolism more active, as well as relieving fatigue, and a music sync low frequency separator including the same.

In addition, the present disclosure is directed to providing a sound source signal separator that can generate a low frequency signal linked to music and perform effective massage or therapy by the low frequency signal, while the user listens to his or her favorite music and low frequency massage or therapy is performed, and a music sync low frequency stimulator including the same. The present disclosure relates to a sound source signal separator for generating a low frequency signal linked to music by separating only a music signal among a plurality of sound source signals, and a music sync low frequency stimulator including the same.

One aspect of the invention provides a music sync low frequency stimulator, including a speaker for outputting a plurality of first sound source signals, a sound source signal separator for separating at least one of the plurality of first sound source signals, a low frequency signal generator for generating a low frequency signal, and a music sync unit for controlling the strength and frequency of the low frequency signal according to at least one of second sound source signals separated by the sound source signal separator.

Herein, the sound source signal separator receives the plurality of first sound source signals from a plurality of sound sources and outputs the same to the speaker, and the second sound source signal is output to the music sync unit.

In addition, the sound source signal separator may block the first sound source signal output to the speaker from being input to the music sync unit.

In addition, the sound source signal separator includes an input terminal to which the plurality of first sound source signals are input, an output terminal from which the plurality of first sound source signals are output, and a first voltage follower provided between the input terminal and the output terminal.

In addition, the first voltage follower is connected between the input terminal, in which the second sound source signal is separated, and the output terminal.

In addition, the first voltage follower includes an operational amplifier, and the sound source and the music sync unit are connected to a non-inverting terminal of the operational amplifier, and the speaker is connected to an inverting terminal of the operational amplifier.

In addition, the music sync low frequency stimulator according to embodiments of the present invention may further include a first sound source signal amplifier connected between the sound source signal separator and the speaker.

In addition, the music sync unit may include a second voltage follower connected to an output node from which the second sound source signal is output.

In addition, the music sync unit may further include a converter for converting an analog sound source signal output from the second voltage follower into a digital sound source signal, and a control unit for outputting a music sync low frequency signal in which the strength and frequency of the low frequency signal are controlled according to the digital sound source signal.

In addition, the music sync unit may further include a second sound source signal amplifier connected between the second voltage follower and the converter.

In addition, the plurality of first sound source signals may include a music signal, a buzzer, and a voice guidance signal.

In addition, the sound source signal separator may separate the music signal from the plurality of first sound source signals and output to the music sync unit.

In addition, the sound source signal separator may receive the music signal by wire or wirelessly from a plurality of sound sources.

In addition, according to embodiments of the present invention provides a sound source signal separator, wherein the sound source signal separator is a sound source signal separator which separates at least one of the plurality of first sound source signals, and outputs at least one separated second sound source signals to a music sync unit, the sound source signal separator including an input terminal to which the plurality of first sound source signals are input, an output terminal from which the plurality of first sound source signals are output; and a first voltage follower connected between the input terminal, in which the second sound source signal is separated, and the output terminal.

Herein, the sound source signal separator may receive the plurality of first sound source signals from a plurality of sound sources and output the same to a speaker, and the second sound source signal may be output to the music sync unit.

In addition, the music sync unit may control the strength and frequency of the low frequency signal according to the second sound source signal.

In addition, the first voltage follower may block a plurality of first sound source signals output to the speaker from being input to the music sync unit.

In addition, the first voltage follower includes an operational amplifier, the sound source and the music sync unit are connected to a non-inverting terminal of the operational amplifier, and the speaker is connected to an inverting terminal of the operational amplifier.

In addition, the plurality of first sound source signals may include a music signal, a buzzer, and a voice guidance signal.

In addition, the sound source signal separator may separate the music signal from the plurality of first sound source signals and output to the music sync unit.

According to embodiments of the present invention, by applying low frequency waves to the human body, it is possible to provide proper stimulation to muscles, blood vessels, and the like, and thus, it is possible to reduce body weight by decomposing body fat in the corresponding area, beautify the body, and promote blood circulation to make metabolism more active, as well as relieving fatigue.

In addition, according to embodiments of the present invention, while all of a music signal, a buzzer, and a voice guidance signal are output to the speaker, the music signal is separated and output to a music sync unit, and thus, the user can thereby receive low frequency massage or therapy while simultaneously listening to his or her favorite music. Also, the buzzer and voice guidance signal are prevented from being reflected in a low frequency signal, thereby generating a low frequency signal linked to music, and effective massage or therapy may be performed through the low frequency signal.

The effects that may be obtained in embodiments of the present invention are not limited to the above-mentioned effects, and other effects not mentioned can be clearly understood by those skilled in the art from the following description.

DETAILED DESCRIPTION OF EMBODIMENTS

Figure 1:
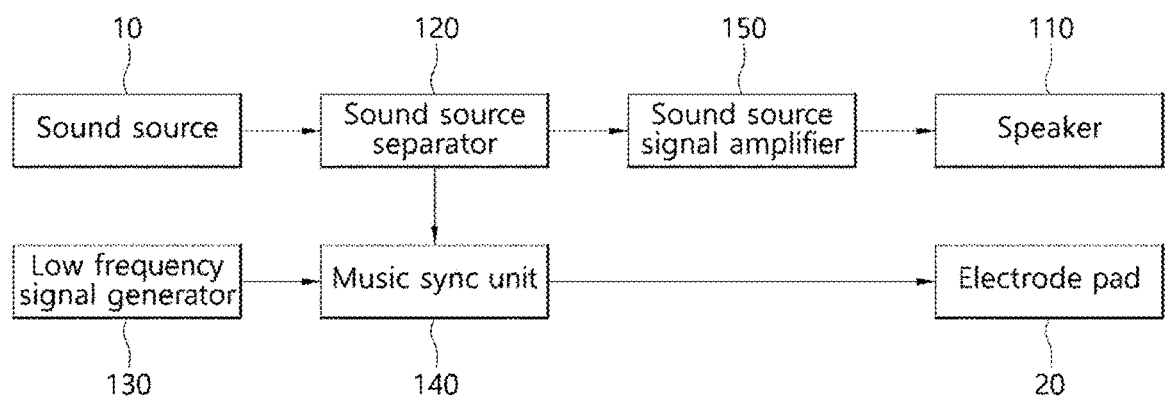
FIG. 1 is a block diagram of a music sync low frequency stimulator according to an embodiment of the present invention.

Hereinafter, embodiments of the present invention will be described in detail with reference to the accompanying drawings. The detailed description to be disclosed hereinafter together with the accompanying drawings is intended to describe embodiments of the present invention and is not intended to represent the only embodiments by which the present invention can be practiced. In the drawings, in order to clearly describe the present invention, parts irrelevant to the description may be omitted, and the same reference numerals may be used for the same or similar constitutional components throughout the specification.

In an embodiment of the present invention, expressions such as "or", "at least one", and the like may represent one of the words listed together or a combination of two or more. For example, "A or B" and "at least one of A and B" may include only one of A or B, and may include both A and B.

FIG. 1 is a block diagram of a music sync low frequency stimulator according to an embodiment of the present invention.

As illustrated in FIG. 1, the music sync low frequency stimulator according to an embodiment of the present invention may be configured to include a speaker 110, a sound source signal separator 120, a low frequency signal generator 130, a music sync unit 140, and a sound source signal amplifier 150.

Herein, the speaker 110 and the sound source signal amplifier 150 may be configured as respective modules or may be configured as one module, and the sound source signal separator 120 and the music sync unit 140 may also be configured as respective modules or may be configured as one module, but are not limited thereto.

The music sync low frequency stimulator according to an embodiment of the present invention includes features of transmitting music through the speaker 110, simultaneously generating a low frequency signal linked to music through the music sync unit 140, and providing the same to the user to perform effective massage or therapy.

Herein, low frequency refers to a low frequency vibration or wave, or refers to an electromagnetic wave at a specific frequency. In the field of communication engineering, an audible frequency in the range of 20 Hz to 20 kHz is considered as low frequency with respect to high frequency used in wireless communication, and in the electromagnetic method, an electromagnetic wave of 30 kHz to 300 kHz is defined as low frequency.

Meanwhile, low frequency of 50 Hz or 60 Hz used for electric power is sometimes referred to as commercial frequency, and such low frequency can be easily generated using a generator, a vacuum tube, a transistor, and the like.

Among these low frequencies, when low frequency of about 1 Hz to 5,000 Hz is applied to the human body, it is possible to provide proper stimulation to muscles, blood vessels, and the like, and thus, it is possible to reduce body weight by decomposing body fat in the corresponding area, beautify the body, and promote blood circulation to make metabolism more active, as well as relieving fatigue.

Hereinafter, the configuration of the music sync low frequency stimulator according to an embodiment of the present invention will be described in detail.

The speaker 110 may output at least one of a plurality of first sound source signals or all of these signals. Herein, the plurality of first sound source signals may include a music signal, a buzzer, and a voice guidance signal.

For example, the music signal may be a signal including various music genres (e.g., classical music, ballad, jazz, etc.). Herein, the user may select his or her favorite music. Unlike the above, music may be automatically selected according to the user's preference based on big data. Also, the buzzer and the voice guidance signal may be signals indicating an operational process of the music sync low frequency stimulator according to an embodiment of the present invention and signals including guidance and explanation for the operational process.

Meanwhile, it is not problematic when the speaker 110 outputs all of the plurality of first sound source signals together, but when all of the plurality of first sound source signals are input to the music sync unit 140, not only the music signal but also the buzzer and the voice guidance signal are reflected in a low frequency signal, and thus, noise is generated when outputting the low frequency signal linked to music. That is, not only a low frequency signal linked to music but also an unnecessary low frequency signal is provided to the user. Accordingly, effective massage or therapy may not be performed.

In order to address the foregoing, the sound source signal separator 120 separates at least one of a plurality of first sound source signals. That is, the sound source signal separator 120 receives a plurality of first sound source signals from a plurality of sound sources 10 and outputs the same to the speaker, but a second sound source signal separated from the plurality of first sound source signals is output to the music sync unit 140.

Specifically, while the sound source signal separator 120 outputs all of a music signal, a buzzer, and a voice guidance signal to the speaker 110, the music signal is separated and output to the music sync unit 140, and thus, it is possible thereby to prevent the buzzer and the voice guidance signal from being reflected in a low frequency signal. Accordingly, a low frequency signal linked to music is generated to perform effective massage or therapy.

Herein, the sound source signal separator 120 blocks a plurality of first sound source signals output to the speaker from being input to the music sync unit 140 again. A sound source 10 may be stored in an internal memory provided inside a music sync low frequency stimulator, an external memory provided outside the music sync low frequency stimulator, or a universal serial bus (USB) memory removable from the music sync low frequency stimulator.

Specifically, a music signal among the plurality of first sound source signals may be output by wire from an internal memory and a USB memory (e.g., MP3), or output wirelessly (e.g., Bluetooth (BT)) from an external memory.

Accordingly, the sound source signal separator 120 may receive a music signal front a plurality of sound sources 10 by wire or wirelessly.

Among the plurality of first sound source signals, a buzzer and a voice guidance signal may be pre-stored in an internal memory by a setter.

Figure 2:
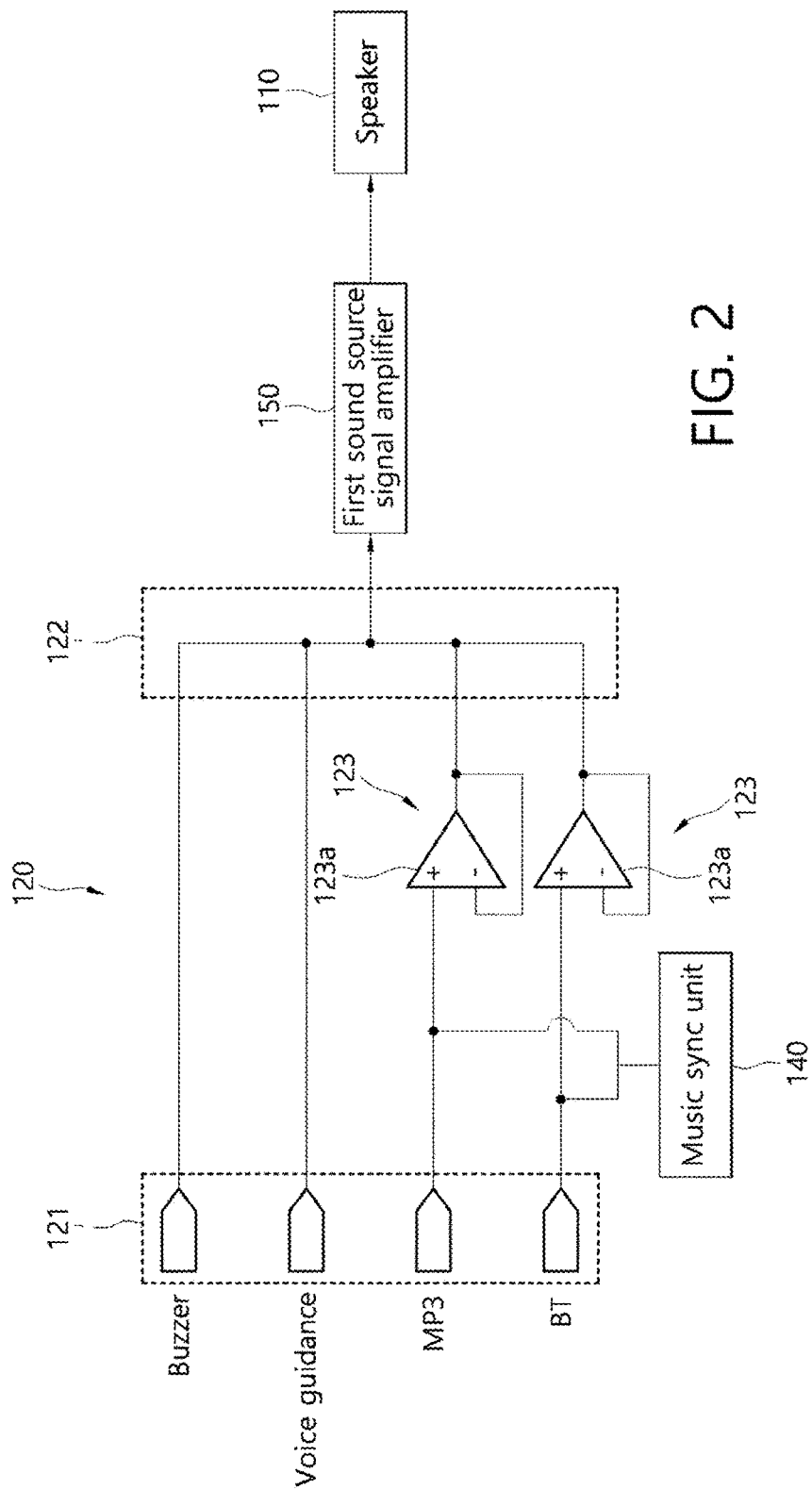
FIG. 2 is a circuit diagram of a sound source signal separator according to an embodiment of the present invention.

FIG. 2 is a circuit diagram of a sound source signal separator according to an embodiment of the present invention.

As illustrated in FIG. 2, the sound source signal separator 120 may be configured to include an input terminal 121 to which a plurality of first sound source signals are input, an output terminal from which a plurality of first sound source signals are output, and a first voltage follower 123 provided between the input terminal 121 and the output terminal 122.

Herein, a music signal (e.g., MP3, Bluetooth (BT)), a buzzer, and a voice guidance signal may be input to the input terminal 121.

The first voltage follower 123 is connected between the input terminal 121, in which a second sound source signal is separated, and the output terminal 122 among a plurality of input and output terminals 121, 122.

Specifically, the first voltage follower 123 may include an operational amplifier (OP-Amp) 123a. Herein, the sound source 10 and the music sync unit 140 are connected to a non-inverting terminal (+) of the operational amplifier 123a, and the speaker is connected to an inverting terminal of the operational amplifier 123a.

The ideal operational amplifier 123a has an input resistance of infinity ($\infty$) and an output resistance of 0.

Herein, the voltage signal of the non-inverting terminal (+) is transmitted to the output terminal of the operational amplifier 123 as it is by the virtual short circuit principle. However, the voltage signal is not transmitted from the output terminal to the non-inverting terminal (+).

As such, while the first voltage follower 123 is connected between the input terminal 121 and the output terminal 122 where a music signal is input and output, it is not connected to the input terminal 121 and the output terminal 122 where a buzzer and a voice guidance signal are input and output.

Accordingly, all of a music signal, a buzzer, and a voice guidance signal are output to the speaker 110, but only a music signal is output to the music sync unit 140. In addition, a buzzer and a voice guidance signal that are output to the output terminal 122 of the first voltage follower 123 are not transmitted to the music sync unit 140.

Meanwhile, an example of the sound source signal separator 120 has been described as a voltage follower 123, but is not limited thereto. A circuit configuration capable of separating and outputting only a music signal among a plurality of first sound source signals and blocking the inflow of a buzzer and a voice guidance signal is sufficient.

A first sound source signal amplifier 150 is connected between the sound source signal separator 120 and the speaker 110. Accordingly, a first sound source signal that has passed through the sound source signal separator 120 may be amplified and transmitted to the speaker, and as the speaker 110 transmits music to the user, the user may receive low frequency massage or therapy while listening to his or her favorite music.

The sound source signal separator 120 separates a music signal from a plurality of first sound source signals to output to the music sync unit 140, and the low frequency signal generator 130 generates a low frequency signal to output the same to the music sync unit 140.

Accordingly, the music sync unit 140 may provide the user with low frequency stimulation linked to music by controlling the strength and frequency of a low frequency signal according to a music signal separated by the sound source signal separator 120.

Herein, the low frequency signal output to the music sync unit 140 is output to an electrode pad 20, and the user may receive massage or therapy according to low frequency stimulation by contacting the electrode pad 20 to the acupuncture points of the human body or to a region where muscle pain is felt.

As such, the music sync low frequency stimulator according to an embodiment of the present invention outputs all of a music signal, a buzzer, and a voice guidance signal to the speaker 110, but separates a music signal to output to the music sync unit 140. Thus, the user may receive low frequency massage or therapy while listening to his or her favorite music, while simultaneously preventing the buzzer and voice guidance signal from being reflected in a low frequency signal. Accordingly, a low frequency signal linked to music is generated thereby, and effective massage or therapy may be performed through this low frequency signal.

Figure 3:
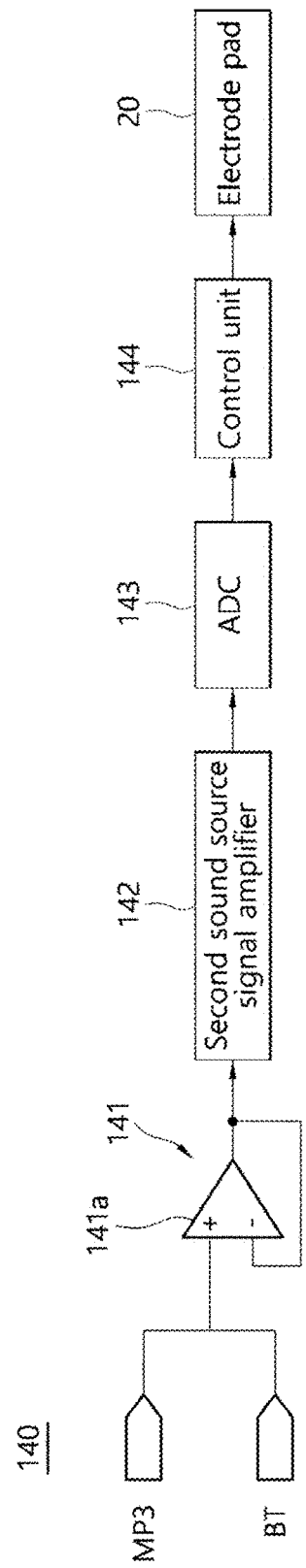
FIG. 3 is a block diagram of a music sync unit according to an embodiment of the present invention.

FIG. 3 is a block diagram of a music sync unit according to an embodiment of the present invention.

As illustrated in Example 3, the music sync unit 140 according to an embodiment of the present invention may be configured to include a second voltage follower 141, a second sound source amplifier 142, a converter 143, and a control unit 144.

The second voltage follower 141 is connected to an output node from which a second sound source signal is output.

Specifically, the second voltage follower 141 may include an operational amplifier 141a. Herein, a second sound source signal is input to a non-inverting terminal (+) of the operational amplifier 141a, and an inverting terminal (−) of the operational amplifier 141a is connected to the output terminal of the operational amplifier 141a.

The ideal operational amplifier 141a has an input resistance of infinity (∞) and an output resistance of 0.

Herein, according to the virtual short circuit principle, a voltage signal of the non-inverting terminal (+), that is, an analog sound source signal is transmitted as it is to an output terminal of the operational amplifier 141a. However, a voltage signal is not transmitted from the output terminal to the non-inverting terminal (+).

As such, the second voltage follower 141 can not only prevent the load effect of the music sync unit 140 to accurately transmit an analog sound source signal, but also can prevent external noise and disturbance generated by the music sync unit 140 from transmitting to the speaker 110.

The converter 143 is an analog-to-digital converter and converts an analog sound source signal output from the second voltage follower 141 into a digital sound source signal.

The control unit 144 outputs a music sync low frequency signal in which the strength and frequency of a low frequency signal are controlled according to a digital sound source signal converted by the converter 143 to the electrode pad 20.

The second sound source signal amplifier 142 is connected between the second voltage follower 141 and the converter 143.

Accordingly, an analog sound source signal passed through the second sound source signal amplifier 142 may be amplified and transmitted to the converter 143, and the converter 143 may convert this analog sound source signal into an accurate digital sound source signal.

Hereinafter, the sound source signal separator 120 according to an embodiment of the present invention will be described with reference to FIGS. 1 to 3.

The sound source signal separator 120 according to an embodiment of the present invention separates at least one of a plurality of first sound source signals and outputs at least one second sound source signals that have been separated to a music sync unit, and may be configured to include an input terminal 121 to which a plurality of first sound source signals are input, an output terminal 122 from which a plurality of first sound source signals are output, and a first voltage follower 123 connected between an input terminal 121, in which a second sound source signal is separated, and an output terminal 122.

Herein, a plurality of first sound source signals may include a music signal, a buzzer, and a voice guidance signal.

The sound source signal separator 120 as such receives a plurality of first sound source signals from a plurality of sound sources and outputs the same to the speaker, but the separated second sound source signal is output to the music sync unit 140.

Herein, the music sync unit 140 controls the strength and frequency of a low frequency signal according to the separated second sound source signal.

The first voltage follower 123 may block a first sound source signal output to the speaker from being input to the music sync unit 140 again.

Specifically, the first voltage follower 123 includes an operational amplifier 123a, and the sound source 10 and the music sync unit 140 are connected to a non-inverting terminal (+) of the operational amplifier 123a, and the speaker 110 is connected to an inverting terminal (−) of the operational amplifier 123a.

With such configuration and connection, the sound source signal separator 120 according to an embodiment of the present invention separates at least one second music signals from a plurality of first sound source signals and outputs to the music sync unit 140.

As such, while the sound source signal separator 120 according to an embodiment of the present invention outputs all of a music signal, a buzzer, and a voice guidance signal to the speaker 110, the music signal is separated and output to the music sync unit 140, and thus, the user may thereby receive low frequency massage or therapy while simultaneously listening to his or her favorite music. Also, the buzzer and voice guidance signal are prevented from being reflected in a low frequency signal, thereby generating a low frequency signal linked to music, and effective massage or therapy may be performed through the low frequency signal.

Embodiments disclosed herein can be implemented or performed by a computing device having at least one processor, at least one memory and at least one communication interface. The elements of a method, process, or algorithm described in connection with embodiments disclosed herein can be embodied directly in hardware, in a software module executed by at least one processor, or in a combination of the two. Computer-executable instructions for implementing a method, process, or algorithm described in connection with embodiments disclosed herein can be stored in a non-transitory computer readable storage medium.

Even though embodiments of the present invention have been described so far, a person of ordinary skill in the art to which the present invention pertains may implement in modified forms without departing from the essential characteristics of the present invention.

The embodiments of the present invention disclosed in the present specification and drawings are only provided for examples to easily explain the technical content of the present invention and to aid understanding of the present invention, and are not intended to limit the scope of the present invention. Therefore, the scope of the present invention should be construed that all changes or modifications derived based on the technical spirit of the present invention are included in the scope of the present invention in addition to the embodiments disclosed herein.

What is claimed is:

1. A music sync low frequency stimulator, comprising:
   a speaker configured to output a plurality of first sound source signals;
   a sound source signal separator configured to separate at least one of the plurality of first sound source signals;
   a low frequency signal generator configured to generate a low frequency signal;
   a music sync unit configured to control the strength and frequency of the low frequency signal according to at least one of second sound source signals separated by the sound source signal separator,
   wherein the sound source signal separator comprises:
   an input terminal to which the plurality of first sound source signals are input;
   an output terminal from which the plurality of first sound source signals are output; and
   a first voltage follower provided between the input terminal and the output terminal.

2. The music sync low frequency stimulator of claim 1,
wherein the sound source signal separator is configured to receive the plurality of first sound source signals from a plurality of sound sources and output the same to the speaker, and
wherein the second sound source signal is output to the music sync unit.

3. The music sync low frequency stimulator of claim 2,
wherein the sound source signal separator is configured to block the first sound source signal output to the speaker from being input to the music sync unit.

4. The music sync low frequency stimulator of claim 1,
wherein the first voltage follower is connected between the input terminal, in which the second sound source signal is separated, and the output terminal.

5. The music sync low frequency stimulator of claim 1,
wherein the first voltage follower comprises an operational amplifier, and
wherein the sound source and the music sync unit are connected to a non-inverting terminal of the operational amplifier, and the speaker is connected to an inverting terminal of the operational amplifier.

6. The music sync low frequency stimulator of claim 1, further comprising a first sound source signal amplifier connected between the sound source signal separator and the speaker.

7. The music sync low frequency stimulator of claim 2,
wherein the music sync unit comprises a second voltage follower connected to an output node from which the second sound source signal is output.

8. The music sync low frequency stimulator of claim 7,
wherein the music sync unit further comprises:
a converter configured to convert an analog sound source signal output from the second voltage follower into a digital sound source signal; and
a control unit configured to output a music sync low frequency signal in which the strength and frequency of the low frequency signal are controlled according to the digital sound source signal.

9. The music sync low frequency stimulator of claim 8,
wherein the music sync unit further comprises a second sound source signal amplifier connected between the second voltage follower and the converter.

10. The music sync low frequency stimulator of claim 2,
wherein the plurality of first sound source signals include a music signal, a buzzer, and a voice guidance signal.

11. The music sync low frequency stimulator of claim 10,
wherein the sound source signal separator is configured to separate the music signal from the plurality of first sound source signals and output to the music sync unit.

12. The music sync low frequency stimulator of claim 10,
wherein the sound source signal separator is configured to receive the music signal by wire or wirelessly from a plurality of sound sources.

13. A sound source signal separator,
wherein the sound source signal separator is a sound source signal separator which is configured to separate at least one of the plurality of first sound source signals, and output at least one separated second sound source signal to a music sync unit, the sound source signal separator comprising:
an input terminal to which the plurality of first sound source signals are input;
an output terminal from which the plurality of first sound source signals are output; and
a first voltage follower connected between the input terminal, in which the second sound source signal is separated, and the output terminal,
wherein the music sync unit is configured to control the strength and frequency of a low frequency signal according to the second sound source signal.

14. The sound source signal separator of claim 13,
wherein the sound source signal separator is configured to receive the plurality of first sound source signals from a plurality of sound sources and output the same to a speaker, and the second sound source signal is output to the music sync unit.

15. The sound source signal separator of claim 14,
wherein the first voltage follower is configured to block the plurality of first sound source signals output to the speaker from being input to the music sync unit.

16. The sound source signal separator of claim 14,
wherein the first voltage follower comprises an operational amplifier, and
wherein the sound source and the music sync unit are connected to a non-inverting terminal of the operational amplifier, and the speaker is connected to an inverting terminal of the operational amplifier.

17. The sound source signal separator of claim 14,
wherein the plurality of first sound source signals include a music signal, a buzzer, and a voice guidance signal.

18. The sound source signal separator of claim 17,
wherein the sound source signal separator is configured to separate the music signal from the plurality of first sound source signals and output to the music sync unit.

* * * * *